(12) United States Patent
Sommer et al.

(10) Patent No.: US 8,509,899 B2
(45) Date of Patent: Aug. 13, 2013

(54) MULTI-ELECTRODE IMPLANTABLE SYSTEMS AND ASSEMBLIES THEREOF

(75) Inventors: John Louis Sommer, Coon Rapids, MN (US); Joseph Michael D'Sa, Woodbury, MN (US); Joyce K. Yamamoto, Maple Grove, MN (US); Brad C. Tischendorf, Minneapolis, MN (US); James D. Reinke, Maple Grove, MN (US); Andrew J. Thom, Maple Grove, MN (US); Thomas P. Miltich, Otsego, MN (US); William John Taylor, Anoka, MN (US); Kenneth C. Gardeski, Plymouth, MN (US); Larry Earl Tyler, Mesa, AZ (US); Jeffrey O. York, Mesa, AZ (US); Gordon O. Munns, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 136 days.

(21) Appl. No.: 13/008,524

(22) Filed: Jan. 18, 2011

(65) Prior Publication Data

US 2012/0165902 A1   Jun. 28, 2012

Related U.S. Application Data

(60) Provisional application No. 61/426,590, filed on Dec. 23, 2010.

(51) Int. Cl.
*A61N 1/362* (2006.01)
(52) U.S. Cl.
USPC .......................................................... 607/37
(58) Field of Classification Search
USPC .................................................... 607/36–38
See application file for complete search history.

(56) References Cited

U.S. PATENT DOCUMENTS

| | | | |
|---|---|---|---|
| 4,579,119 | A | 4/1986 | Callaghan |
| 4,628,934 | A | 12/1986 | Pohndorf et al. |
| 5,175,067 | A | 12/1992 | Taylor et al. |
| 5,306,581 | A | 4/1994 | Taylor et al. |
| 5,336,253 | A | 8/1994 | Gordon et al. |

(Continued)

FOREIGN PATENT DOCUMENTS

| | | |
|---|---|---|
| EP | 0 518 364 A2 | 12/1992 |
| WO | WO 00/25664 | 5/2000 |

OTHER PUBLICATIONS (PCT/US2011/034455) PCT Notification of Transmittal of the International Search Report and the Written Opinion of the International Searching Authority, Apr. 29, 2011.

*Primary Examiner* — Rex R Holmes
(74) *Attorney, Agent, or Firm* — Reed A. Duthler

(57) ABSTRACT

Hermetically sealed assemblies, for example, that include IC chips, are configured for incorporation within a connector terminal of an implantable medical electrical lead, preferably within a contact member of the terminal. An assembly may include two feedthrough subassemblies, welded to either end of the contact member, to form an hermetic capsule, in which an IC chip is enclosed, and a tubular member, which allows a lumen to extend therethrough, along a length of the terminal. A multi-electrode lead may include multiplexer circuitry, preferably a switch matrix element and a communications, control and power supply element that are electrically coupled to the contact member and to another contact member of the terminal. Each pair of switch matrix switches allows for any two of the electrodes to be selected, in order to deliver a stimulation vector, via stimulation pulses from a device/pulse generator, to which the connector terminal is connected.

11 Claims, 11 Drawing Sheets

(56) References Cited

U.S. PATENT DOCUMENTS

| | | |
|---|---|---|
| 5,411,024 A | 5/1995 | Thomas et al. |
| 5,513,793 A | 5/1996 | Malmgren |
| 5,750,926 A | 5/1998 | Schulman et al. |
| 5,796,044 A | 8/1998 | Cobian et al. |
| 5,968,086 A | 10/1999 | Bonner et al. |
| 6,144,866 A * | 11/2000 | Miesel et al. ............ 600/333 |
| 6,824,521 B2 | 11/2004 | Rich et al. |
| 7,190,245 B2 | 3/2007 | Receveur et al. |
| 7,286,884 B2 | 10/2007 | Marshall et al. |
| 7,493,174 B2 | 2/2009 | Belalcazar et al. |
| 7,525,298 B2 | 4/2009 | Morgan et al. |
| 2008/0312726 A1 | 12/2008 | Frank et al. |
| 2009/0321107 A1 | 12/2009 | Taylor et al. |

* cited by examiner

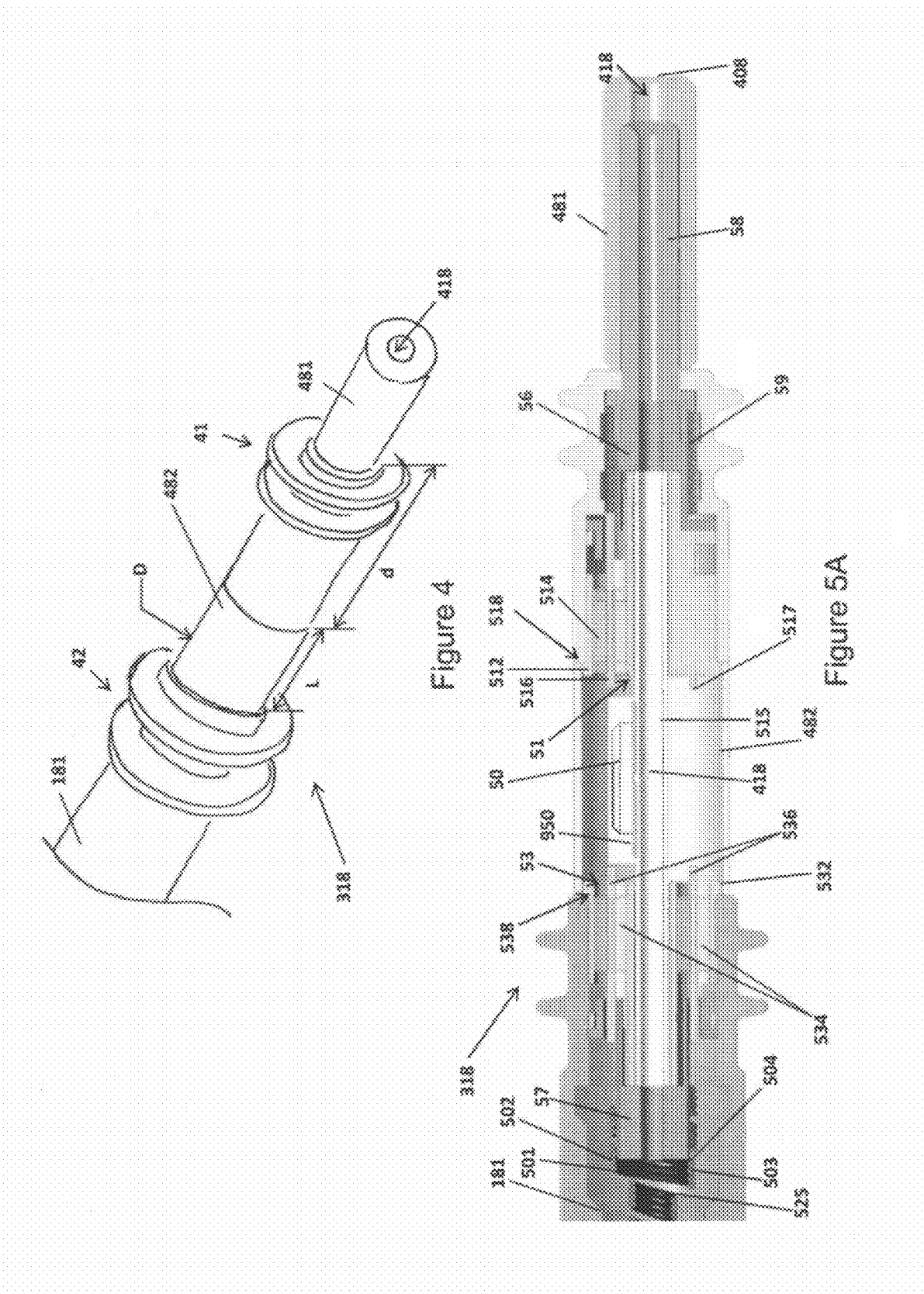

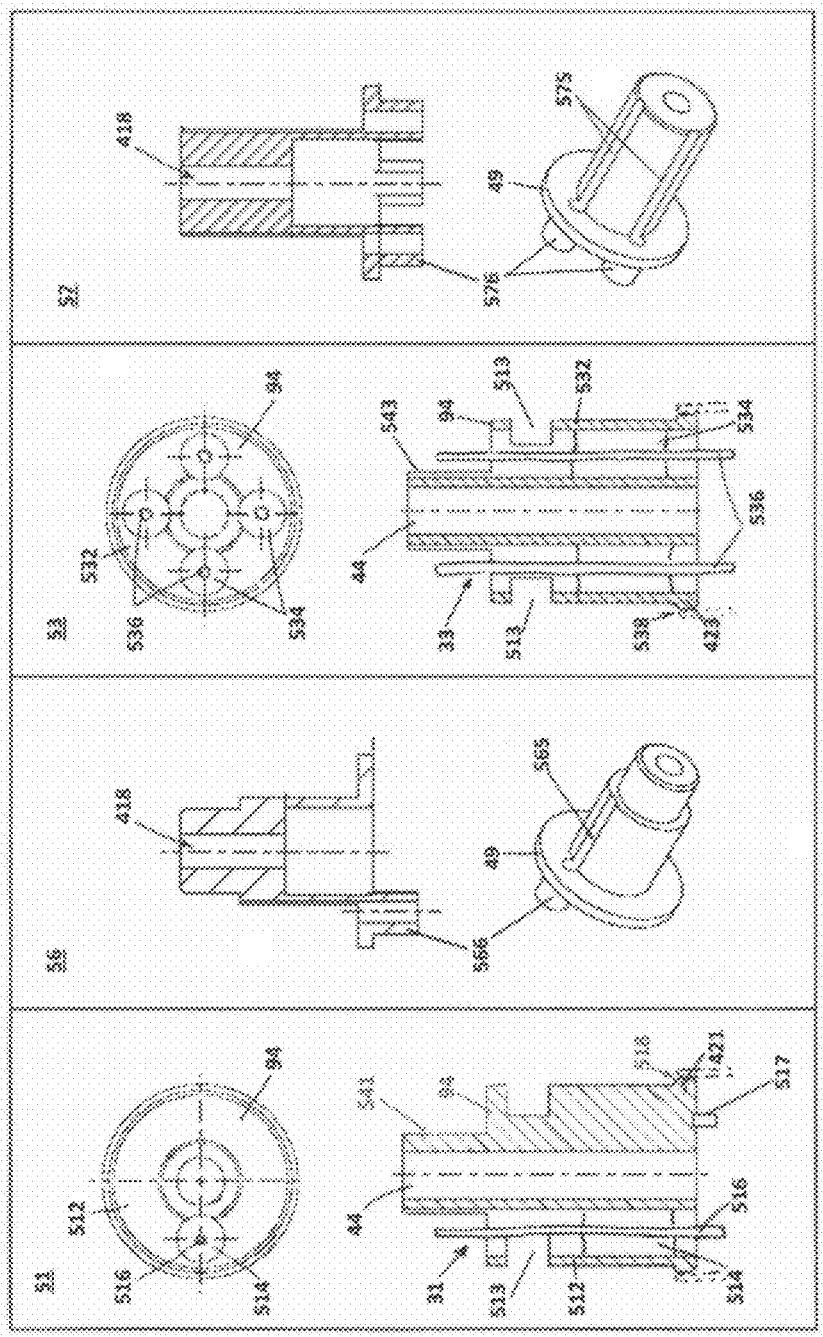

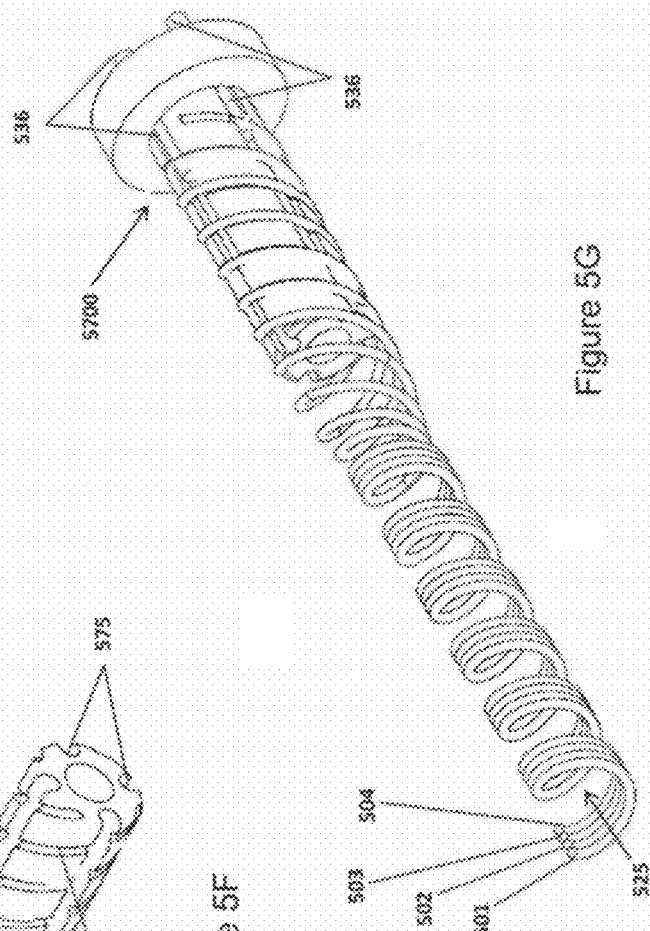

MULTI-ELECTRODE IMPLANTABLE SYSTEMS AND ASSEMBLIES THEREOF

CROSS-REFERENCE TO RELATED APPLICATIONS

This application claims the benefit of U.S. Provisional Application No. 61/426,590, filed on Dec. 23, 2010. The disclosure of the above application is incorporated herein by reference in its entirety.

TECHNICAL FIELD

The present invention pertains to medical electrical stimulation and sensing, and more particularly to implantable systems that include an elongate medical electrical lead having multiple electrodes and integrated circuitry.

BACKGROUND

Providing effective medical electrical stimulation, for example, in cardiac pacing or neuromodulation, relies, at least in part, upon properly locating implantable medical electrodes within a patient's body. Implantable electrodes are typically mounted on distal portions of implantable medical electrical leads, and proximal connector terminals of the leads are configured for coupling with implantable devices/pulse generators that include electronics and a power supply for providing the stimulation pulses to the electrodes. An implantable lead may include a pair of electrodes and a corresponding pair of elongate conductors, wherein each conductor is coupled to a corresponding electrode and extends proximally therefrom, within an elongate insulative body of the lead, to the connector terminal thereof. Implanting the lead in the patient's body, such that the pair of electrodes is properly positioned to deliver an effective bipolar stimulation vector, and/or to effectively sense electrical activity within the patient's body, may be somewhat challenging and/or time consuming. So, if the lead includes more than two electrodes from which to select a most effective pair, after the lead is positioned for implant within the body, the positioning of the lead may be significantly less tedious.

Furthermore, implantable leads that include a plurality of electrodes from which to select provide greater flexibility for stimulation therapy in general. However, in order to maintain certain standard connections between implantable leads and devices, wherein a standard/limited number of device contacts and corresponding device feedthroughs correspond to a standard/limited number of lead connector terminal contacts, some means for coupling a selected subset of the plurality of lead electrodes to the corresponding limited number of lead connector contacts is required. Although various means for selectively coupling one or two of a plurality of electrodes of an implanted lead to the electronic circuitry of the device, to which the connector terminal of the lead is coupled, has been taught in the past, there is still a need for new and improved designs to facilitate the selective coupling.

SUMMARY

The present disclosure sets forth specific system configurations and associated new and improved designs for hermetically sealing switching circuitry, and/or other types of circuitry, which are incorporated within the structure of medical electrical leads, in particular within the connector terminals thereof. Embodiments of the present invention encompass various designs for hermetically sealing integrated circuit (IC) chips within a connector terminal of an implantable medical electrical lead. According to some embodiments, an hermetic capsule is formed by an electrical contact member, of the lead connector terminal, and at least two feedthrough subassemblies. Alternately, or in addition to the hermetic capsule, an hermetic package formed, at least in part, by a ceramic insulator, encloses the IC chip(s). According to some embodiments, a distal one of the two feedthrough subassemblies is preferably configured to facilitate a strain-relieved junction between feedthrough pins of the subassembly and multiple coiled conductors of the lead within the connector terminal thereof.

Multi-electrode medical electrical leads, according to some embodiments, include a switching assembly formed by two feedthrough subassemblies and a multiplexer, which facilitates the selection of a subset of electrodes from a plurality of electrodes mounted on the lead, and, preferably, the polarity of each of the electrodes in the selected pair. A lead connector terminal, according to some embodiments, includes the switching assembly mounted within an electrical contact member of the connector terminal, which contact member is electrically isolated and spaced apart, distally, from another electrical contact member of the terminal, and the multiplexer is electrically coupled to each of the contact members. The multiplexer preferably includes a switch matrix element and a communications, control and power supply (CCP) element, wherein the switch matrix includes a pair of switches corresponding to each conductor that is coupled to and extends from a corresponding electrode of the plurality of electrodes; a first of each pair of switches is adapted to connect and disconnect the corresponding conductor to/from one of the aforementioned contact members and the CCP element, and a second of each pair of switches is adapted to connect and disconnect the corresponding conductor to/from the other of the aforementioned contact members and the CCP element.

Some preferred configurations of the switching assembly are such that the lead connector terminal, in which the switching assembly is mounted, maintains conformance to a particular industry standard, for example, that which is commonly known as the IS-1 standard, in order to ensure compatibility of connection of the connector terminal to any implantable pulse generator, from a variety of manufacturers, which is designed for IS-1 connector compatibility. Preferred configurations of the switching assembly also allow for a lumen to extend along a length of the lead connector terminal such that a proximal opening into the lumen provides for passage of an elongate instrument, such as a guide wire or a stylet, into a longitudinally extending internal channel of the lead, for example, in order to facilitate delivery/implant of the lead.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings wherein like numerals denote like elements.

FIG. 4 is a perspective view of a lead connector terminal which may be employed by the system of FIG. 1, according to some preferred embodiments.

FIG. 5A is a longitudinal cross-section view of the connector terminal of FIG. 4, according to some embodiments.

FIG. 5B presents an end view and longitudinal cross-section view of a proximal feedthrough subassembly employed by the connector terminal of FIGS. 4 and 5A, according to some embodiments.

FIG. 5C presents a perspective view and a longitudinal cross-section view of a proximal support member employed by the connector terminal of FIGS. 4 and 5A, according to some embodiments.

FIG. 5D presents an end view and a longitudinal cross-section view of a distal feedthrough subassembly employed by the connector terminal of FIGS. 4 and 5A, according to some embodiments.

FIG. 5E presents a perspective view and a longitudinal cross-section view of a distal support member employed by the connector terminal of FIGS. 4 and 5A, according to some embodiments.

FIG. 5F is a perspective view of an alternate embodiment of a distal support member.

FIG. 5G is a perspective view of a junction including the distal support member of FIG. 5F, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions and manufacturing processes are provided for selected elements, and all other elements employ that which is known to those skilled in the field of the invention. Those skilled in the art will recognize that some of the examples may have suitable alternatives.

Figure 1:
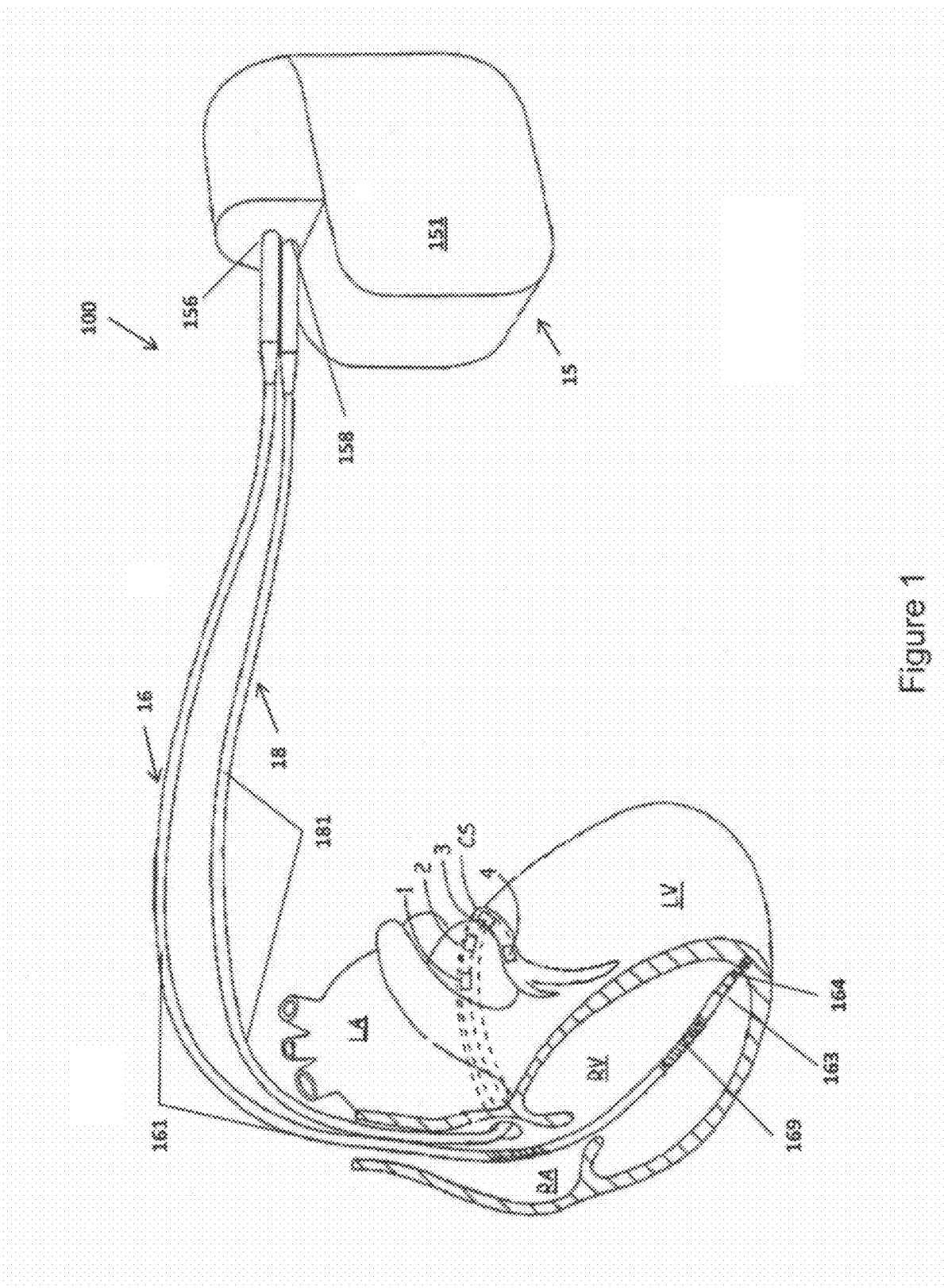
FIG. 1 is a schematic depicting an implanted medical electrical stimulation system, which may employ embodiments of the present invention.

FIG. 1 is a schematic depicting an implanted medical electrical stimulation system 100, which may employ embodiments of the present invention. FIG. 1 illustrates system 100 including an implantable device/pulse generator 15, also known as an implantable cardioverter defibrillator (ICD), and two elongate implantable medical electrical leads 16, 18 coupled thereto and extending therefrom into a heart in order to deliver pacing and defibrillation stimulation pulses from device 15. According to FIG. 1, each of leads 16, 18 includes a connector terminal which is inserted within a corresponding connector port 156, 158 of device 15 for electrical coupling with electrical contacts of the device, mounted therein and coupled, via an hermetic feedthrough assembly, to electronic circuitry and a power source of device 15, which are contained with an hermetically sealed housing 151 of device 15. FIG. 1 further illustrates an insulative body 181 of lead 18 extending into a coronary sinus CS of the heart for pacing and sensing of a left ventricle LV thereof, via any one or two of a plurality of electrodes 1, 2, 3, 4, which are mounted on a distal portion of insulative body 181. Although not shown in FIG. 1, it should be understood that, according to embodiments of the present invention, each of electrodes 1, 2, 3, 4 is coupled to a corresponding elongate conductor that extends through insulative body 181 to the connector terminal of lead 18. Likewise each of electrodes 163, 164 and 169, of lead 16, is coupled to a corresponding elongate conductor that extends in an insulative body 161 of lead 16 to the connector terminal thereof.

Figure 2:
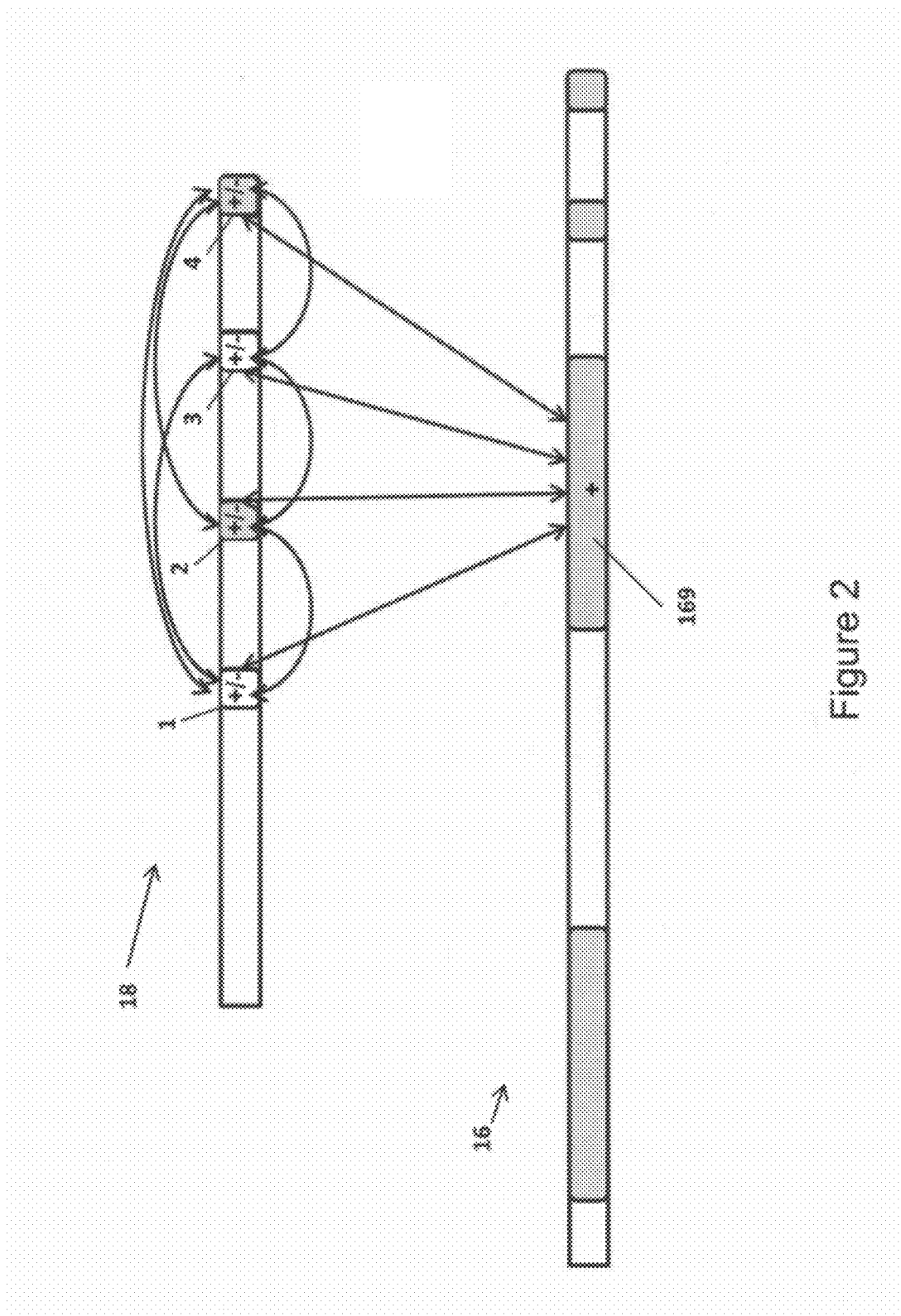
FIG. 2 is a schematic depicting multiple alternative stimulation vectors that may be delivered by the implanted system shown in FIG. 1, according to some embodiments of the present invention.

With further reference to FIG. 1, electrodes 163 and 164 may be utilized for low voltage pacing and sensing of a right ventricle RV of the heart, while electrode 169 is illustrated as a high voltage electrode, which, in conjunction with housing 151 of device 15, is positioned to deliver high voltage shocks for defibrillation therapy of the heart. According to some embodiments of the present invention, electrode 169 may also be employed along with one of electrodes 1, 2, 3, 4 of lead 18 to deliver pacing stimulation to the left ventricle LV. FIG. 2 is a schematic depicting multiple alternative stimulation vectors that may be delivered, via system 100, in order to pace the left ventricle LV, according to some embodiments of the present invention. FIG. 2 illustrates four alternative stimulation vectors that include electrode 169, as an anode, with any one of electrodes 1, 2, 3, 4, as a cathode, and twelve alternative vectors that include any two of electrodes 1, 2, 3, 4 of opposite polarity. It should be noted that, according to some embodiments, system 100 need only include lead 18, in which case, the total number of stimulation vectors from which to select is twelve, unless lead 18 includes more than the four illustrated electrodes, as lead 18 may, according to further embodiments. Alternately, lead 18 may only include three electrodes, in which case, without lead 16, the total number of vectors from which to select is reduced to six.

As was mentioned above, implanting a lead in order to properly position a pair of electrodes of the lead for effective bipolar stimulation, and/or sensing, can sometimes be challenging and time consuming, particularly when the lead is delivered transvenously through the coronary sinus CS for left ventricular pacing, similar to that shown in FIG. 1, or even deeper within the coronary venous vasculature. Thus, the option to select a pair of electrodes, from among a plurality of electrodes included on a single lead, as well as the polarity of each electrode in the pair, in order to deliver a particular stimulation vector, for example, as depicted in FIG. 2, can make implanting the lead significantly less tedious. With further reference to FIG. 1, those skilled in the art will appreciate that electronic switching may be integrated into the circuitry of device 15, or that an integrated circuit, which includes switching may be built into lead 18, in order to allow the selection of one or two of electrodes 1, 2, 3, 4 for pacing, via application of a particular stimulation vector, so that a separate and complete circuit for each of electrodes 1, 2, 3, 4 is not necessary in system 100. Such switching, in general, has been taught, but the present disclosure sets forth specific system configurations and associated new and improved designs for hermetically sealing switching circuitry, and/or other types of circuitry, which are incorporated within the structure of medical electrical leads, in particular within the connector terminals thereof.

Figure 3:
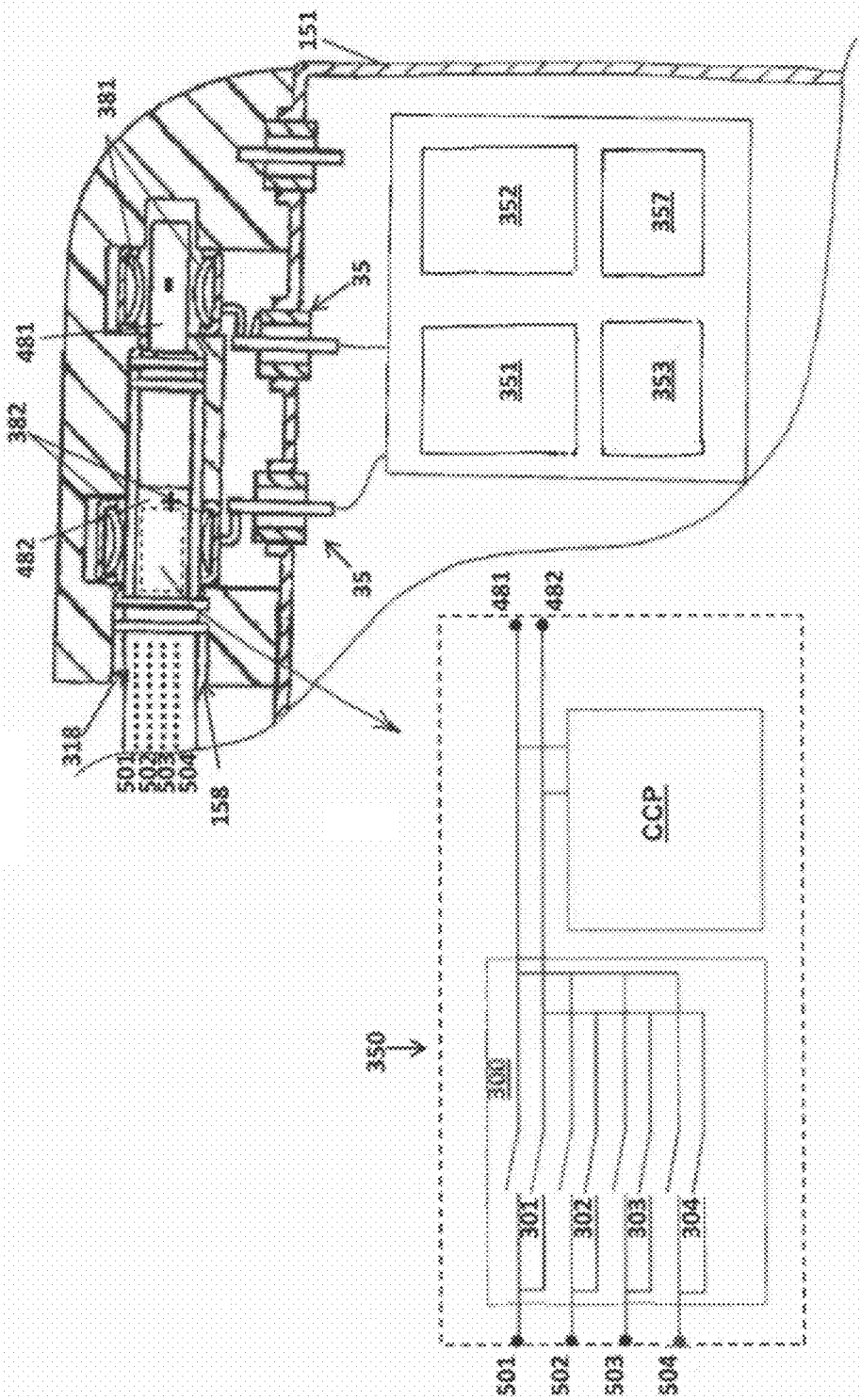
FIG. 3 is a schematic including block diagrams representing electronics associated with a device and lead, for example, included in the system of FIG. 1, according to some embodiments of the present invention.

FIG. 3 is a cross-section schematic including block diagrams associated with a connector terminal 318 of an implantable medical lead and an implantable medical device, to which the lead is coupled, for example, lead 18 and device 15, respectively, of FIG. 1; the illustrated block diagrams represent electronics that enable selection of a stimulation vector from the multiple alternative vectors shown in FIG. 2, according to some preferred embodiments of the present invention. FIG. 3 illustrates connector terminal 318 inserted within connector bore 158 of device 15 such that first and second electrical contact members 481, 482 thereof are positioned for electrical coupling with first and second electrical device contact 381, 382, respectively. As was alluded to above, each of device contacts 381, 382 is coupled, via hermetic feedthroughs 35, to an electronics module contained within housing 151, which module may include a microcontroller 351, a communications unit 352, a clock 353 and a power supply 357. FIG. 3 further illustrates dashed lines to designate a preferred location of a multiplexer 350 within connector terminal 318, which is part of a switching assembly that will be described in greater detail below.

According to the illustrated embodiment, the polarity of each of device contacts 381, 382 is established such that first connector contact member 481 is set as a cathode and second connector contact member 482 is set as an anode. Furthermore, connector terminal 318 preferably conforms to the industry standard, ISO 5841-3:2000, for low-profile connectors of implantable pacemakers, which is more commonly known as the "IS-1 standard", in order to be compatible with any implantable pulse generator, from a variety of manufacturers, which is designed to be compatible with IS-1 connectors. The IS-1 standard specifies essential dimensions and performance requirements related to connector fit, and, with reference to FIG. 4, which is a perspective view of lead connector terminal 318, some of the essential dimensions are: a diameter D and a length L of second contact member 482; and a distance d that defines a spacing between first contact member 481 and second contact member 482. (FIG. 4 further illustrates a proximal set of sealing rings 41, to provide electrical isolation between contact members 481, 482, within connector bore 158, and a distal set of sealing rings 42 to isolate the inserted connector terminal 318, in particular, contact member 482, from the implant environment external to bore 158.) Thus, preferred embodiments of the switching assembly, which includes multiplexer 350, are designed to fit within the structure of connector terminal 318, without impacting the conformance of connector terminal 318 to the IS-1 standard. Furthermore, the multiplexer circuitry itself is preferably compatible with connection to the low voltage IS-1 standard-compatible port of an ICD, such as device 15, and is robust enough to withstand damage that could be induced by electrosurgery, external defibrillation shocks, and internal defibrillation shocks.

With reference to the block diagram of multiplexer 350 in FIG. 3, multiplexer 350 includes a switch matrix element 300, which has four pairs of switches 301, 302, 303, 304, one pair corresponding to each electrode 1, 2, 3, 4, and a communications, control and power supply (CCP) element. Multiplexer 350 is preferably mounted on a silicon chip that is contained within second contact member 482, for example, an integrated circuit (IC) chip 50, which is shown in FIG. 5A. Switch matrix 300 may be a micro electromechanical (MEMS) switch, for example, constructed similar to that described in commonly assigned U.S. Pat. No. 7,190,245, entitled "Multi-stable Micro Electromechanical Switches and Methods of Fabricating Same", which is hereby incorporated by reference. According to FIG. 3, each pair of switches 301-304 is coupled to a corresponding conductor 501, 502, 503, 504 for electrical connection with the corresponding electrode 1, 2, 3, 4; a first switch of each pair of switches 301-304 is capable to connect or disconnect the corresponding conductor to first connector contact 481 and to CCP element, and a second switch of each pair is capable to connect or disconnect the corresponding conductor to second connector contact 482 and to CCP element. CCP element includes a communications port, to receive messages/instructions and to acknowledge the received messages/instructions, switch control circuitry, to drive gates of the switches on and off, according to programming instructions, a capacitor, to store power to operate the multiplexer electronics, and a rectifier, to recover power from the lead. It should be understood that multiplexer 350 preferably further includes protection circuitry, for example, to prevent damage to the multiplexer electronics during high current transients, and test circuitry to verify operation of the electronics during production testing.

According to some embodiments, switch matrix 300 may be employed by lead 18 to provide some fault tolerance by functioning, in response to conductor impedance measurements, to disconnect a faulty conductor and connect an alternate conductor in its place, thereby connecting the corresponding alternative electrode, of electrodes 1-4. According to some alternate embodiments, an implantable medical electrical lead that includes one or more electrodes and at least two elongate conductors for each electrode, employs switch matrix 300 to disconnect a faulty conductor of two or more conductors connected to a particular electrode, in response to impedance measurements, and connect an alternate conductor of that electrode.

Biphasic pulses from device 15 may be used to provide power as well as provide data/instructions to multiplexer 350. According to some preferred embodiments, the communications port of CCP element is adapted for a relatively simple communication scheme that employs biphasic data pulses, wherein data bits are encoded via the order of the positive and negative pulses. Either sub-threshold biphasic power pulses, or the pacing pulses themselves, delivered from device 15 through contacts 381, 382, may power multiplexer 350. For example, pacing pulses of 1.5 V and 0.5 ms, at a minimum rate of approximately 30 bpm, may be sufficient to maintain a power supply to multiplexer 350; but, if pacing pulses are insufficient in amplitude or are not present, the biphasic power pulses may be employed, wherein each phase of the biphasic power pulse is less than or equal to approximately 5 μs (3 μs typical) in duration and less than approximately 3.5V in amplitude, so that positive and negative pulse amplitudes seen at the lead electrodes will match to within +/−10% to prevent stimulation. Commonly assigned U.S. Pat. Nos. 7,493,174 and 7,525,298, which are hereby incorporated by reference, describe in greater detail communications and power supply schemes that may be employed by embodiments of the present invention, according to methods known to those skilled in the art.

A connected, or enabled, switch of switch matrix 300 preferably passes pacing pulses and lead impedance measurement pulses between −9V and +4.5V on first connector contact member 481 relative to second connector contact member 482, while a disconnected, or disabled, switch should, preferably, block voltages between −9V and +4.5V on the corresponding electrode, relative to the voltage of second contact member 482. Furthermore, enabled switches preferably pass sensing signals, in the absence of pacing pulses, and allow sensing of an evoked response to pacing pulses. According to some embodiments, a default setting of switch matrix element 300 connects conductor 504, which corresponds to most distal electrode 4, to first connector contact 481, and conductor 502, which corresponds to electrode 2, to second connector contact 482, when a spacing between electrodes 4 and 2 is approximately 20 mm. At the time of implant, each of the stimulation vectors is, preferably, evaluated, in order to select a pair for stimulation therapy; alternate pairs of electrodes may also be evaluated, separately, for sensing and, based upon, for example, R-wave amplitude, a different pair may be selected for sensing. A pace sense analyzer (PSA) may be employed for this evaluation, in conjunction with a special interface box that is connected between the PSA and lead 18 in order to provide power to multiplexer 350, in the absence of pacing pulses, and to provide the ability to select among the electrodes 1, 2, 3, 4. Co-pending and commonly assigned patent application Ser. No. 12/893,517, filed on Sep. 29, 2010 and entitled "Prioritized Programming of Multi-Electrode Pacing Leads", which is hereby incorporated by reference, describes methods/routines, which may be automated, for evaluating alternate stimulation vectors for left ventricular pacing, according to predetermined criteria such as stimulation efficacy and stimulation efficiency.

If, for example, with reference to system 100 of FIG. 1, pacing pulses are delivered from device 15 to the right ventricle RV, through electrodes 163 and 164 of lead 16, switches of switch matrix 300 remain closed/enabled while both of first and second device contacts 381, 382 are disconnected within device 15, allowing first and second connector contact members 481, 482 of lead 18 to float. Thus, voltage from lead 16, which couples into electrodes 1,2, 3, 4 of lead 18, may inject a charge into the power supply storage capacitor of the CCP element. However, the injected charge should be low enough so that it does not result in cross-chamber stimulation. Likewise, in the event that lead 18 is abandoned and capped off (i.e. first and second connector contact members 481, 482 isolated from the body in which lead 18 is implanted), an injected charge from other stimulating electrodes should not result in cross-chamber stimulation.

Table 1, below, provides exemplary target specifications for multiplexer electronics, according to some embodiments of the present invention.

TABLE 1

| Parameter | Minimum | Typical | Maximum | Units |
| --- | --- | --- | --- | --- |
| Switch on resistance | | | 10 | ohms |
| Charge injected into LV electrode (1, 2, 3, 4) during RV pace. (contact members 481, 482 floating, 1 V pulse applied between any electrode pair) | | | 10 | nC |
| Charge injected into "floating" LV electrode (1, 2, 3, 4) during an LV pace. (contact members 481, 482 and 2 LV electrodes driven to 9 V, other 2 LV electrodes driven to 0 V and 9 V) | | | 100 | nC |
| Pacing or power pulse rate | 0.5 | 1 | | Hz |
| Voltage range which must be passed | −9 | | +4.5 | V |
| Power pulse amplitude | +/−2 | | +/−3.5 | V |
| Power pulse width (each phase) | 2.5 | 3.3 | 5 | µs |

TABLE 1-continued

| Parameter | Minimum | Typical | Maximum | Units |
| --- | --- | --- | --- | --- |
| Gap between positive and negative phases | 2.5 | 3.3 | 5 | µs |
| Gap between adjacent power pulses | 2.5 | 3.3 | 5 | µs |

Turning now to FIG. 5A, a more detailed view of the construction of the switching assembly within lead connector terminal 318, according to some embodiments, may be seen in a longitudinal cross-section view of connector terminal 318. In particular, FIG. 5A illustrates a proximal feedthrough subassembly 51 and a distal feedthrough subassembly 53, which, in conjunction with second contact member 482, form an hermetic capsule that encloses IC chip 50, on which multiplexer 350 is mounted. According to the illustrated embodiment, proximal feedthrough assembly 51 includes a feedthrough pin 516, a ferrule 512 and an insulator 514, which is hermetically sealed to pin 516 and to ferrule 512 and which isolates pin 516 from ferrule 512; ferrule 512 is shown welded to a proximal end of second contact member 482, as designated by reference numeral 518. It should be understood that electrical coupling of second contact member 482 to the hermetically enclosed multiplexer 350 is accomplished via this direct coupling to ferrule 512 at 518. FIG. 5B presents an end view and longitudinal cross-section view of proximal feedthrough subassembly 51, wherein an optional weld ridge 421 of ferrule 512 is shown extending about a perimeter thereof for mating within a perimeter of the proximal end of second contact member 482, which is shown with dashed lines, and for the welding of ferrule 512 to contact member 482 at 518. FIG. 5A further illustrates feedthrough pin 516 coupled to a conductive jumper 59 that in turn is coupled to a conductive core 58 to which first connector contact member 481 is coupled, in order to provide electrical connection between first contact member 481 and the hermetically enclosed multiplexer 350. With further reference to FIG. 5A, distal feedthrough assembly 53 includes a plurality of feedthrough pins 536, a ferrule 532 and an insulator 534, which is hermetically sealed to each of pins 536 and to ferrule 532 and which isolates pins 536 from one another and from ferrule 532; ferrule 532 is shown welded to a distal end of second contact member 482, as designated by reference numeral 538. FIG. 5D presents an end view and longitudinal cross-section view of distal feedthrough subassembly 53, wherein a weld ridge 423 of ferrule 532 is shown extending about a perimeter thereof for mating within a perimeter of the distal end of second contact member 482, which is shown with dashed lines, and for the welding of ferrule 532 to contact member 482 at 538. Although not shown in FIG. 5A, a distal portion 33 of each of feedthrough pins 536, as designated in FIG. 5D, is preferably directly coupled to a corresponding conductor of the plurality of conductors 501, 502, 503, 504, each of which, in turn, is coupled to a corresponding electrode 1, 2, 3, 4 (FIG. 1), in order to provide electrical connection between electrodes 1, 2, 3, 4 and the hermetically enclosed multiplexer 350.

According to some exemplary embodiments, ferrules 512, 532 and second connector contact member 482 are each formed from a Titanium alloy, preferably Titanium grade 5; other materials from which ferrules 512, 532 and second contact member 482 may be formed include, without limitation, Niobium (Nb), or alloys thereof, stainless steel, MP35N alloy and platinum-iridium alloy. Each feedthrough pin 516, 536 is formed from a metal, such as Tantalum (Ta), Nb, Titanium (Ti), Platinum (Pt), Iridium (Ir), or alloys thereof, but preferably from Nb or a Ti—Nb alloy. Each insulator 514, 534 may be formed from glass or ceramic, but preferably from glass. According to some preferred embodiments, each insulator 514, 534 is formed of the glass composition that is disclosed in commonly-assigned patent application, publication US 2009/0321107, which is hereby incorporated by reference, for example, being about 30% $B_2O_3$, about 20% CaO, about 20% MgO, about 5% $La_2O_3$, about 10% $SiO_2$ and about 15% $Al_2O_3$, wherein percentages are mole percentages, and the CaO and/or MgO may be replaced with corresponding amounts of SrO. These glass insulators 514, 534, known as LaBor 4 glass, are preferably employed with the aforementioned Ti grade 5 ferrules and Ti—Nb alloy pins, and formed and sealed to the corresponding ferrules and feedthrough pins according to methods taught in US 2009/0321107; and, as described in the '107 reference, these insulators have a coefficient of thermal expansion (CTE), which is closer to that of the metals forming pins 516, 536 and ferrules 512, 532, for example, Ti, Nb, Pt, Ir and alloys thereof. According to some alternate embodiments, the glass insulator is Ta-23 glass or Cabal-12 glass, for example, as described in commonly-assigned U.S. Pat. No. 5,306,581, which is hereby incorporated by reference. If ferrules 512, 532 are formed from MP35N alloy, and pins 516, 536 from Ta or Nb, then insulators 514, 534 are preferably formed from Ta-23 glass (nominally 45 weight % $SiO_2$, 20 weight % $Al_2O_2$, 8 weight % $B_2O_3$, 12 weight % CaO, 6 weight % MgO and 2 weight % $La_2O_3$), as described in commonly assigned U.S. Pat. No. 5,175,067, which is hereby incorporated by reference. A length of the seal interface between each of the preferred glass insulators 514, 534 and the corresponding ferrule 512, 532 and pin 516, 536 is preferably greater than approximately two times a diameter of the pin, which pin diameter may be approximately 0.008 inch, according to some preferred embodiments. It should be noted that, although insulator 534 of distal feedthrough subassembly 53 is shown divided up into a plurality of individual insulators, one for each pin 536, in alternate embodiments, insulator 534 may be a single and continuous member that extends around all of pins 536.

With further reference to FIGS. 5B and 5D, a minimum spacing of each insulator 514, 534 from the corresponding welding location 518, 538 is such that heat generated during the welding of ferrules 512, 532 does not compromise the hermetic seal between insulators 514, 534 and pins 516, 536. According to exemplary embodiments that employ the aforementioned preferred glass composition (described in the incorporated '107 reference) as insulators 514, 534, along with the aforementioned Ti grade 5 for ferrules 512, 532, the minimum spacing between the insulators and weld locations is preferably approximately 0.005 inch. According to those embodiments which conform to the IS-1 standard, and with reference back to FIG. 4, second connector contact member 482 is formed as a ring having a length L of approximately 0.160 inch, an outer diameter D of approximately 0.105 inch and an inner diameter of approximately 0.095 inch, such than an outer diameter of each of weld ridges 421, 423 is approximately 0.094 inch to fit within the inner diameter and thereby provide an area for welding of ferrules 512, 532 to member 482, as illustrated.

With reference back to FIG. 5A, in conjunction with FIGS. 5B-E, a proximal insulative support member 56 is shown mounted on a protrusion 541 of ferrule 512 that extends proximally from insulator 514, and a distal insulative support member 57 is shown mounted on a protrusion 543 of ferrule 532 that extends distally from insulators 534. FIG. 5C presents a perspective view and a longitudinal cross-section view of proximal insulative support member 56; and FIG. 5E presents a perspective view and a longitudinal cross-section view of distal insulative support member 57. Each support member 56, 57 is preferably formed from a relatively rigid plastic material, such as durometer 75D polyurethane, which is known to those skilled in the art, and includes a flange 49 that abuts a shoulder 94 of the corresponding ferrule 512, 532, when mounted thereon. FIG. 5C illustrates proximal support member 56 including a channel 565, to receive a proximal portion 31 of feedthrough pin 516 (FIG. 5B), and a protruding sleeve 566 that extends around pin 516 within ferrule 512, just proximal to insulator 514; and FIG. 5E illustrates distal support member 57 including a plurality of channels 575, each of which to receive distal portion 33 of the corresponding feedthrough pin 536 (FIG. 5D), and a plurality of protruding sleeves 576, each of which extends around a corresponding pin 536 within ferrule 532. FIGS. 5B and 5D illustrate ports 513 formed in ferrules 512, 532, which may provide access to backfill, for example, with a silicone medical adhesive, around pins 516, 536 and sleeves 566, 576.

According to some preferred embodiments, conductive jumper 59 wraps around proximal support member 56 and overlays proximal portion 31 of feedthrough pin 516, which extends within channel 565, for coupling thereto, for example, by laser welding. Likewise, according to some preferred embodiments, each of conductors 501, 502, 503, 504 wrap around distal support member 57 such that each conductor 501, 502, 503, 504 overlays a distal portion 33 of the corresponding feedthrough pin 536 within the corresponding channel 575 for coupling thereto, for example, by laser welding or crimping methods known in the art. Suitable materials, from which jumper 59 and each of conductors 501, 502, 503, 504 may be formed, include, without limitation, Nb, or alloys thereof, Tantalum and MP35N alloy. It should be noted that, according to the illustrated embodiment of FIG. 5A, each conductor 501, 502, 503, 504 includes an insulative jacket, for example, formed from any suitable fluoropolymer or polyimide, to electrically isolate each conductor from the other; and a portion of the jacket is removed from a proximal end of each conductor 501, 502, 503, 504, for example, by laser ablation or mechanical stripping, prior to forming the electrical coupling with the corresponding feedthrough pin 536. Electrical isolation of the couplings is achieved by staggering the proximal ends of conductors 501, 502, 503, 504 along a length of support member 57 and backfilling, for example, with silicone medical adhesive, around the couplings.

FIG. 5F is a perspective view of a distal support member 5700, which may be incorporated in place of the above-described support member 57 (FIG. 5E), according to some alternate embodiments. FIG. 5F illustrates distal support member 5700 including channels 575, similar to member 57, which are sized to receive distal portions 33 of feedthrough pins 536. FIG. 5F further illustrates distal support member 5700 including helically formed channels 585, which extend along the same surface in which channels 575 are formed, and by which conductors 501, 502, 503, 504 may be separated and held to facilitate individual coupling of each to the corresponding feedthrough pin 536, for example as is illustrated in FIG. 5G. With reference to FIG. 5A in conjunction with FIG. 5G, conductors 501-504 are wound together as an elongate multi-conductor coil that extends along a length of lead body 181 and forms a longitudinally extending internal channel 525 of a given diameter within lead 18. According to the illustrated embodiments, conductors 501-504 are expanded to a larger diameter in order to fit, within helical channels 585 such that support member 5700 not only facilitates the coupling of each to the corresponding feedthrough pin 536, but also provides strain relief to the coiled conductors 501-504 at the junction therewith.

FIG. 5A further illustrates lead connector terminal 318 including a lumen 418 that extends along a length of terminal 318 and is in fluid communication with longitudinally extending internal channel 525 of lead 18. With reference to FIG. 5A, it may be appreciated that portions of various components of terminal 318 make up an inner wall that forms lumen 418, which inner wall isolates lumen 418 from the switching assembly and all the electrical connections thereof. A proximal opening 408 into lumen 418 provides for passage of an elongate instrument (not shown), for example, a stylet or a guide wire, into internal channel 525. With reference back to FIG. 1, internal channel 525 preferably extends to a distal tip of lead 18, and lumen 418 and channel 525 are useful for positioning of electrodes 1-4 of lead 18 within the coronary sinus CS, for example, by providing a passageway for a guide wire to be maneuvered and advanced ahead of lead 18, according to methods known in the art, and/or for a stylet to be advanced within lead, in order to stiffen the distal portion of lead body 181, to prevent buckling thereof when positioning electrodes 1-4, according to methods known to those skilled in the art. According to FIG. 5A, a portion of lumen 418 is formed by a tubing member 515, which extends between proximal feedthrough subassembly 51 and distal feedthrough subassembly 53, being mounted in longitudinally extending thru-holes 44 (FIGS. 5B and D) of the ferrules 512, 532 thereof. Tubing member 515, according to some preferred embodiments, is formed from metal, such as stainless steel, titanium or tantalum, and each end of member 515 is welded to each of ferrules 512, 532, for example, at protrusions 541, 543 thereof. Lumen 418 is further formed by inner walls of contact member 481, conductive core 58, proximal support member 56 and distal support member 57 and, according to the illustrated construction, is isolated from the hermetically enclosed portions of the switching assembly and the electrical couplings of proximal portion 31 of feedthrough pin 516 and distal portions 33 of feedthrough pins 536.

According to an exemplary embodiment: each thru-hole 44 of ferrules 512, 532 has a diameter of approximately 0.023 inch, as does each bore which accommodates insulators 514, 534; an outer diameter of ferrules 512, 532, along a majority of a length thereof, is approximately 0.088 inch; and the outer diameter of each of weld ridges 421, 423 is approximately 0.094 inch, as indicated above. It should be noted that, although a particular arrangement of feedthrough pins 536 within ferrule 532 is illustrated, an alternate arrangement, wherein all of pins 536 are located on a same side of the longitudinal axis of the part may be employed and will still allow for the aforementioned minimum spacing of insulators 514, 534 from weld locations 518, 538 and for passage of lumen 418 through ferrules 512, 532. Furthermore, any other suitable arrangement is not outside the scope of the present invention, for example, although lumen 418 is shown aligned along a central longitudinal axis of lead connector terminal 318, lumen 418 may be offset therefrom, for example to accommodate other arrangements of feedthrough pins 516, 536.

Figure 5H:
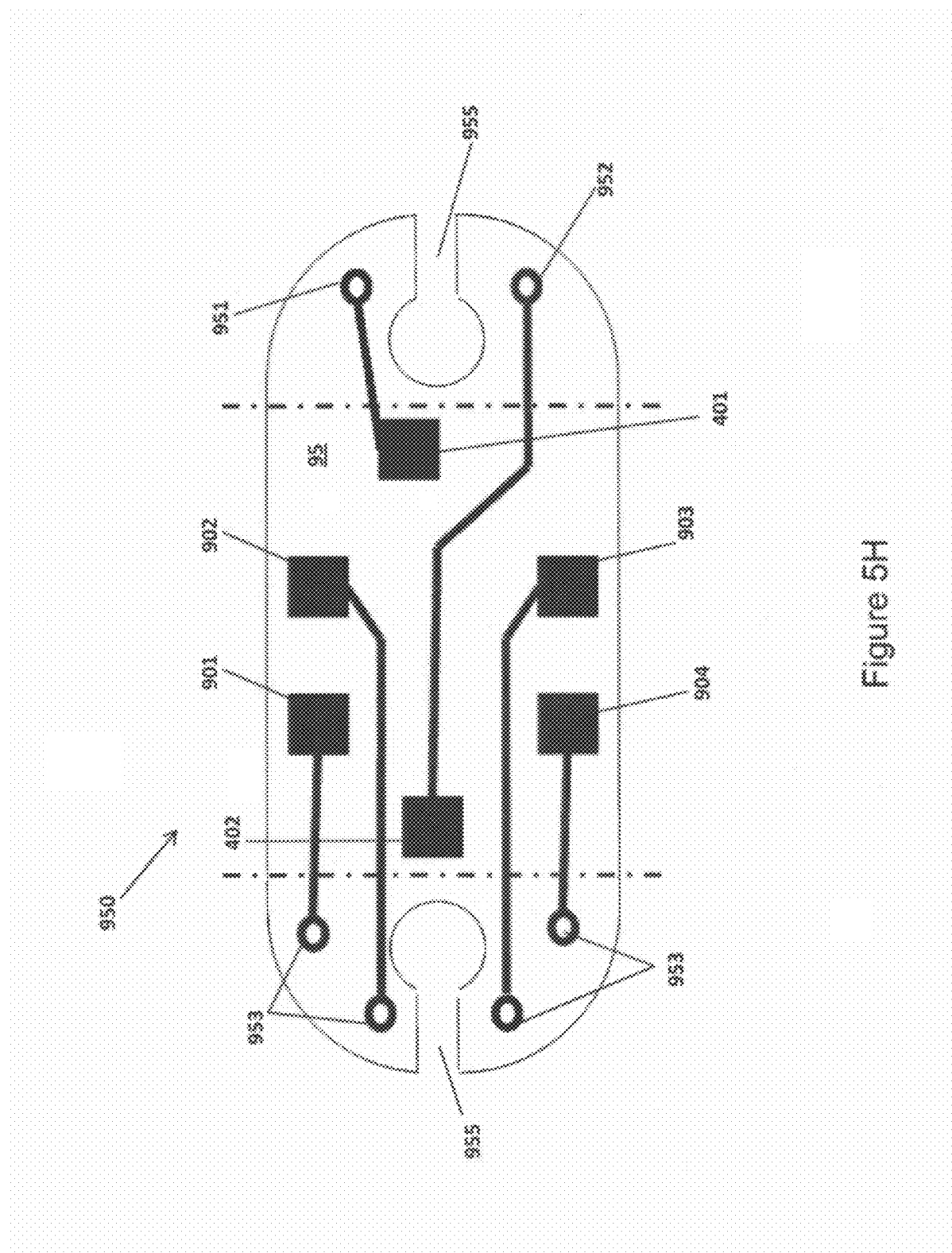
FIG. 5H is a plan view of a flex circuit interface, which may be employed by the connector terminal of FIG. 5A to electrically couple an integrated circuit chip to the feedthrough subassemblies, according to some embodiments.

Heretofore electrical couplings of multiplexer 350/IC chip 50 within the hermetically sealed enclosure of the switching assembly have not been described. According to some embodiments a flex circuit interface is employed for these couplings. FIG. 5H is a plan view of a flex circuit 950, according to one embodiment, which may be employed by the connector terminal of FIG. 5A to electrically couple IC chip 50 to feedthrough subassemblies 51, 53. FIG. 5H illustrates flex circuit 950 including conductive traces formed on surface of a substrate 95 thereof, wherein each trace extends from a corresponding contact/bond pad 901-904, 401, 402 to a corresponding connection junction 951, 952, 953. FIG. 5H further illustrates contoured slots 955, which are formed in either end of substrate 95 and sized to fit around tubing member 515, when the ends are folded inward, for example, along the dashed lines of FIG. 5H. With reference back to FIG. 5A, it may be appreciated that, within the hermetic enclosure of the switching assembly, IC chip 50 abuts the illustrated surface of flex circuit 950 such that contact/bond pads 901-904, 401, 402 are electrically coupled to the appropriate terminals of multiplexer 350 (FIG. 3), and the ends of substrate 95 are positioned around tubular member 515, by means of slots 955, such that connection junctions 951 and 952 are positioned for coupling to feedthrough pin 516 and feedthrough ferrule 512, respectively, and each of connection junctions 953 is positioned for coupling to the corresponding feedthrough pin 536. Thus, first connector contact member 481 is electrically coupled to an input terminal of multiplexer 350 via contact/bond pad 401, second contact member 482 to another input terminal of multiplexer 350 via contact/bond pad 402, and each of lead conductors 501, 502, 503, 504 to a corresponding output terminal of multiplexor 350 via the corresponding contact/bond pad 901, 902, 903, 904. According to some preferred embodiments, each of connection junctions 951, 952, 953 are formed by apertures and gold plated traces extending thereabout, wherein each of pins 536 is inserted within the aperture of the corresponding connection junction 953 and brazed/soldered thereto, and pin 516 is inserted within the aperture of connection junction 951 and brazed/soldered thereto. With reference back to FIGS. 5A-B, ferrule 512 of proximal feedthrough assembly 51 may further include a pin protrusion 517 for insertion within the aperture of connection junction 952 for brazing/soldering thereto. It should be noted that, according to alternate embodiments, ferrule 532 of distal feedthrough assembly 53 may alternately include pin protrusion 517 for coupling to flex circuit 950, if connection junction 952 is relocated to the opposite end of substrate 95.

According to some methods of the present invention, initial steps for assembling the switching assembly, described above, include forming feedthrough subassemblies 51, 53 and coupling IC chip 50 to flex circuit 950 (or to one of the alternative substrates that is described below, in conjunction with FIGS. 6 and 7A-B). IC chip 50 may be coupled to flex circuit 950 according to methods known in the art, for example, by brazing/soldering each contact of chip 50 to the corresponding contact/bond pad 401, 402, 901-904. As was mentioned above, in order to form subassemblies 51, 53, glass insulators 514, 534 may be formed and sealed to the corresponding ferrules 512, 532 and feedthrough pins 516, 536, according to methods known in the art, for example, as taught in US 2009/0321107. In subsequent steps, each feedthrough subassembly 51, 53 may be mounted on tubing member 515 and then ferrules 512, 532 welded to member 515 such that weld ridges 421, 423 are spaced apart from one another at a distance that approximately corresponds to length L of second contact member 482 (FIG. 4), for subsequent welding of member 482 to each ferrule 512, 532. Alternately, one of ferrules 512, 532 may be mounted on and welded to tubing member 515, prior to assembling the corresponding feedthrough pin(s) and forming the corresponding glass insulator(s) to complete one of feedthrough subassemblies 51, 53 with tubing member 515 attached thereto. According to some preferred embodiments, each end of tubing member 515 is welded to the end of the corresponding protrusion 541, 543 of the respective ferrule 512, 532, prior to mounting insulative support members 56, 57 onto the corresponding protrusion 541, 543. However, according to some alternate assembly methods, each support member 56, 57 is insert molded onto the corresponding ferrule 512, 532 prior to attaching tubing member 515 thereto, which case, tubing member 515 may be welded to each of ferrules 512, 532 at the end opposite to protrusion 541, 543, in proximity to weld ridges 421, 423.

Once feedthrough subassemblies 51, 53 and tubing member 515 are joined together, the coupled IC chip 50 and flex circuit 950 may be positioned between the spaced apart feedthrough subassemblies 51, 53, for electrical coupling thereto. Flex circuit 950 is preferably attached to tubing member 515, as was described above, prior to forming each electrical coupling with subassemblies 51, 53. However, according to some methods, the coupled IC chip 50 and flex circuit 950 is attached to tubing member 515 prior to welding tubing member 515 to feedthrough subassemblies 51, 53. Finally, once the coupled IC chip 50 and flex circuit 950 is secured between and electrically coupled to feedthrough subassemblies 51, 53, second contact member 482 is passed over subassemblies 51, 53, tubing member 515, and IC chip 50, and positioned for welding each of the proximal and distal ends thereof to the corresponding ferrule weld ridge 421, 423. Thus, the welding of the proximal and distal ends of second contact member 482 completes an hermetic capsule that encloses IC chip 50 and the electrical couplings thereto, according to some preferred embodiments. According to some alternate embodiments, for example, as described below, an alternative or additional hermetic enclosure of IC chip 50 may be formed within second contact member 482.

Figure 6:
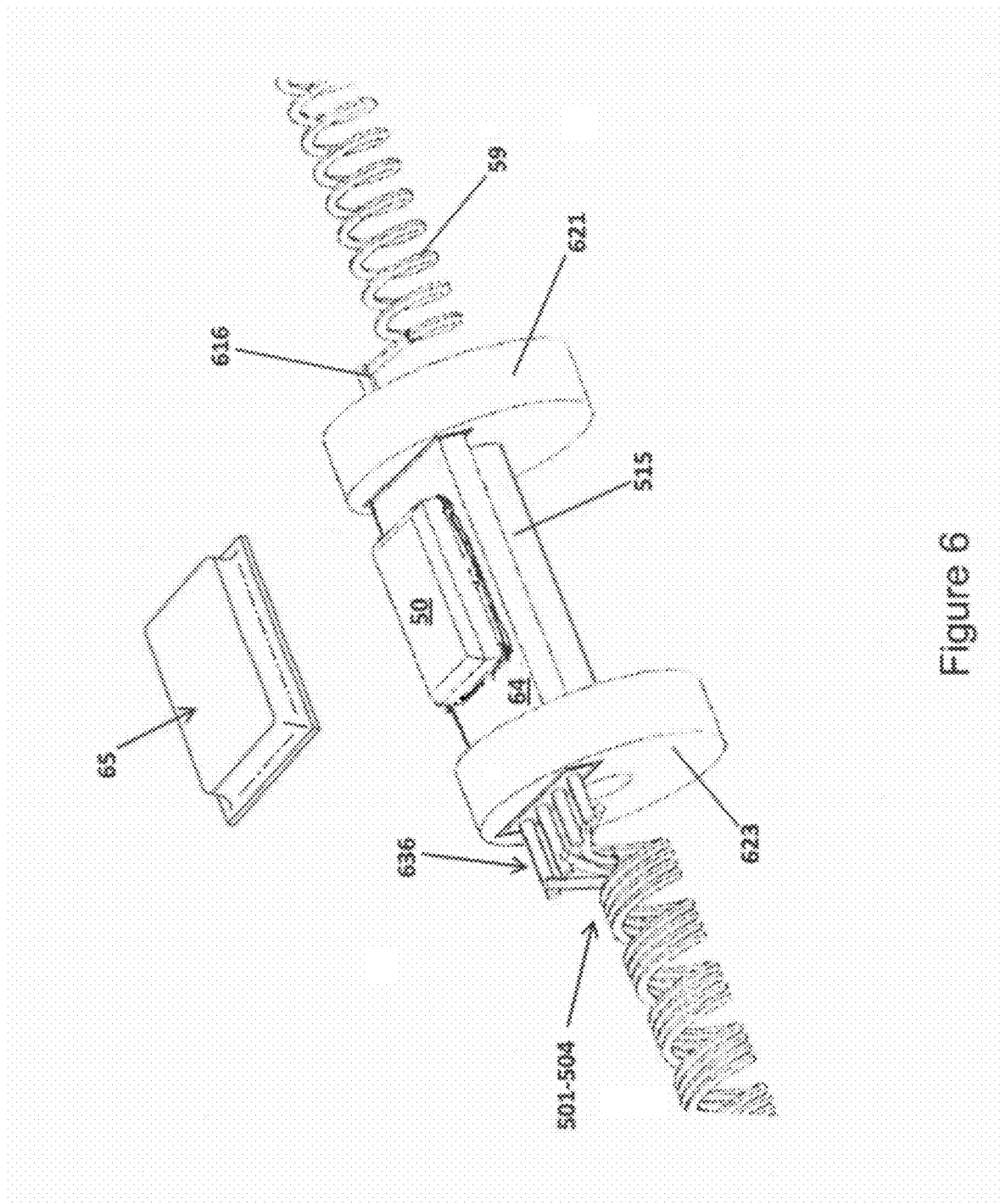
FIG. 6 is a perspective view of a portion of a lead connector terminal, according to some alternate embodiments.

FIG. 6 is a perspective view of a portion of a lead connector terminal, including a switching assembly, according to some alternate embodiments. FIG. 6 illustrates a feedthrough subassembly of the switching assembly including a ceramic insulator 64 that extends between a proximal end plate 621 and a distal end plate 623, and to which a proximal feedthrough pin 616 and a plurality of distal feedthrough pins 636 are hermetically sealed. Each end plate 621, 623 may itself form a ferrule for the feedthrough subassembly or include a separate ferrule welded thereto, and end plates 621, 623 are preferably sized to fit within corresponding ends of second contact member 482 (FIG. 4), for coupling thereto, for example, via laser welding. End plates 621, 623 may further include thru-holes (like thru-holes 44 of ferrules 512, 532) to support tubing member 515, which forms a portion of lumen 418 of the connector terminal (FIG. 4).

FIG. 6 further illustrates ceramic insulator 64 acting as a substrate to support IC chip 50. With reference to FIG. 6, it should be understood that insulator 64 includes a plurality of contact/bond pads formed on an exterior surface thereof, to which IC chip 50 is coupled, and that insulator 64 further includes conductive vias extending therein to electrically couple each feedthrough pin 616, 636 to a corresponding contact/bond pad, and an additional conductive via for coupling proximal end plate 621 to the corresponding contact/bond pad, in order to electrically couple pins 616, 636 and second contact member 482, respectively, to IC chip 50. Insulator 64 is preferably hermetically sealed to each of distal feedthrough pins 636 and proximal feedthrough pin 616 and to each end plate 621, 623, and, according to some embodiments, end plates 621, 623 are welded to ends of second contact member 482, about an entire perimeter thereof (as was described for ferrules 512, 532 of FIG. 5A), in order to form an hermetic capsule around IC chip 50. According to an exemplary embodiment: ceramic insulator 64 is formed from alumina ($Al_2O_3$) with platinum vias and contact/bond pads; pins 616, 636 are formed from Nb, or any of the other suitable materials listed above for pins 516, 536; and ferrules/end plates 621, 623 are formed from the aforementioned Titanium grade 5, or any of the alternate materials mentioned above for ferrules 512, 532. Other suitable insulating materials for insulator 64 include, without limitation, magnesium oxide (MgO), Silica ($SiO_2$), Calcium Oxide (CaO), zirconium oxide ($ZrO_4$) and Yittria ($Y_2O_3$), as well as any suitable combination thereof, or other inorganic elements assemble in a single crystal or polycrystalline or amorphous structure. A particular embodiment of insulator 64 may be a multi-layer structure fabricated and assembled, either prior to a high temperature densification process or after the densification process, wherein a final structure of insulator 64 is characterized by a relatively rigid and chemically inert substrate with metal vias extending therein and/or surface metal traces for electrically coupling IC chip 50 to conductors 501-504. It should be noted that a co-fired multi-layer ceramic/metal process or conventional ceramic packaging technology may be employed to form insulator 64 including the conductive vias and contact/bond pads; and we also contemplate that Laser Additive Manufacturing methods could be employed to fabricate this type of ceramic insulator for embodiments of the present invention.

Similar to the previously-described embodiment, first contact member 481 is electrically coupled to IC chip 50 via conductive jumper 59, which is coupled to proximal feedthrough pin 616, and the proximal segment of each of lead conductors 501-504 is electrically coupled to IC chip 50 via a corresponding one of distal feedthrough pins 636. According to some alternate embodiments, external contact/bond pads may terminate each conductive via of insulator 64 for each of the junctions with the corresponding lead conductors 501-504 and jumper 59, at respective distal and proximal facing surfaces of insulator 64, as an alternative to feedthrough pins 616, 636.

With further reference to FIG. 6, an optional metal cap 65, for example, made of Ti, is shown, and, according to some embodiments, cap 65 may be positioned over the electrically coupled IC chip 50 and, in order to form an hermetic enclosure around IC chip 50, bonded to insulator 64, for example, by a diffusion bonding technique known in the art, for example, as described in U.S. Pat. No. 5,513,793, or by glassing and brazing techniques known in the art. Alternately, a metal frame (not shown) may be formed in insulator 64, by diffusion bonding prior to attaching IC chip 50, in order to surround the coupled IC chip 50, and, then, cap 65 is laser welded to the frame to hermetically enclose IC chip 50, for example, as described in U.S. Pat. No. 5,750,926. Such a metal frame is preferably formed from a Ti—Nb alloy and cap 65 may be formed of Ti, stainless steel or MP35N alloy. In either case, when cap 65 is employed, the above-described welding of ferrule end plates 621, 623 to second contact member 482 may be a redundant hermetically sealed interface, or the requirement of hermetic sealing at this weld interface may be lifted.

Figure 7A:
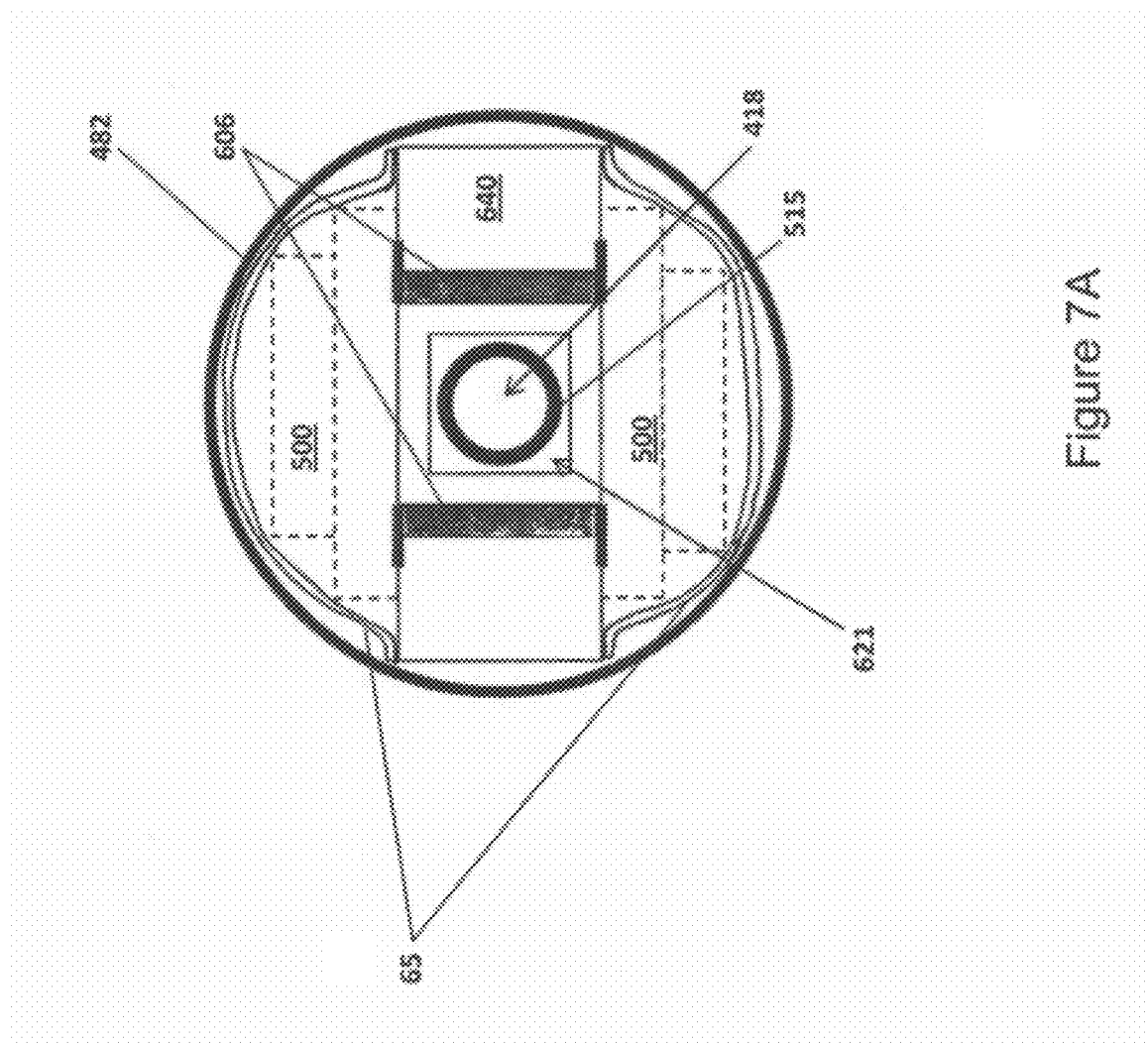
FIG. 7A is a radial section view through a portion of a lead connector terminal, according to yet further embodiments.

FIG. 7A is a radial cross-section view through second contact member 482 (FIG. 4) of a connector terminal in which a pair of titanium caps 65 are employed to enclose a pair of IC chip stacks 500. FIG. 7A illustrates chip stacks 500 coupled on either side of a ceramic insulator substrate 640 that is configured around lumen 418, which may be formed at least in part by the tubing member 515; in order to electrically couple stacks 500 to one another, ceramic insulator substrate 640 includes a pair of conductive vias 606 that may be co-fired therewith for hermetic sealing thereto. Insulator substrate 640 may further include feedthrough pins, hermetically sealed therein, and coupled to corresponding conductive vias, formed therein, wherein the pins extend out through corresponding ferrule end plates at either end of connector contact member 482, for example, like pins 616, 636 shown in FIG. 6, in order couple to corresponding lead conductors 501-504 and jumper 59 to chip stacks 500. Alternately, conductive vias may terminate in contact/bond pads, which are formed on exposed surfaces of substrate 640, outside second contact member 482, for direct coupling with lead conductors 501-504 and jumper 59. Insulator substrate 640 including the conductive vias and contact/bond pads, may be formed by any of the processing techniques described above for insulator 64. Insulator substrate 640 may be formed in two parts, which are bonded together around tubing member 515, and a void 621, between substrate 640 and tubing member 515, may be filled with epoxy in order to secure substrate 640 to tubing member 515.

Figure 7B:
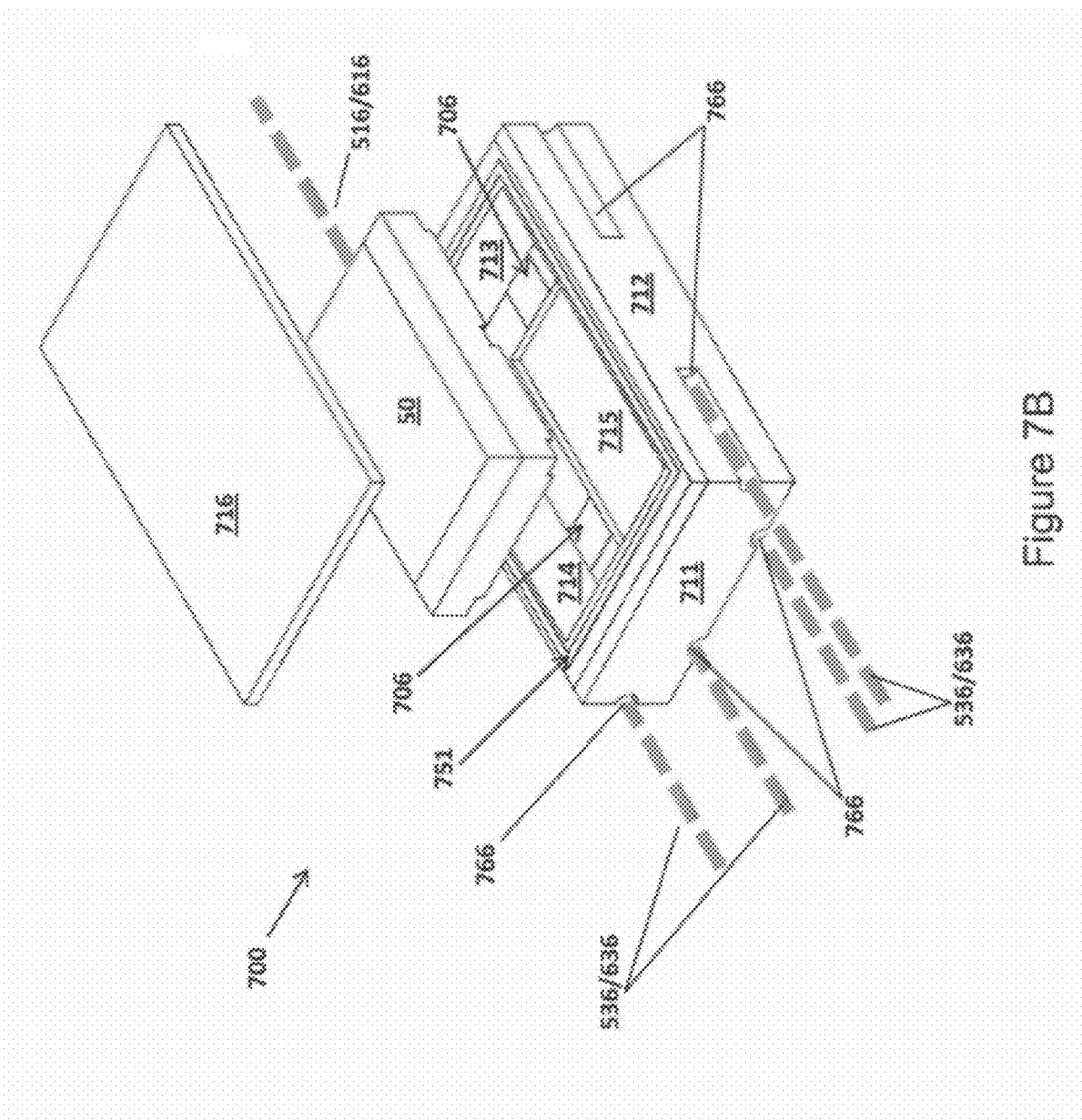
FIG. 7B is an exploded perspective view of an hermetic package that may be employed by some embodiments.

FIG. 7B is an exploded perspective view of a package 700 which may be substituted for insulator 64 in the assembly illustrated in FIG. 6, or integrated within the switching assembly described, above, in conjunction with FIGS. 5A-G, without the need for flex circuit 950 of FIG. 5H, according to various alternate embodiments. FIG. 7B illustrates package 700 including ceramic sidewalls 711-715, contact/bond pads 706, which are formed an inner surface of sidewall 715, and conductive interconnect members 766 in the form of metalized grooves, which are formed on an exterior surface of sidewalls 712, 714 and 715. According to the illustrated embodiment, IC chip 50 is coupled to contact/bond pads 706, when enclosed within package 700, and each contact/bond pad 706 is electrically coupled to one of the conductive interconnect members 766, by a corresponding conductive via (not shown) that extends within the corresponding sidewall. According to some preferred embodiments, ceramic sidewalls 711-715 are formed from alumina, in which conductive vias are formed, for example, being co-fired with the alumina for hermetic sealing therebetween. Contact/bond pads 706 and the metallic film lining each groove 766 may be formed from any suitable conductive material, which is, preferably, biocompatible and biostable, for example, comprising one or more of: platinum, gold, niobium, titanium, palladium, tantalum, iridium, and alloys thereof. According to some embodiments, in which second contact member 482 and feedthrough subassemblies 51, 53 form a hermetic capsule around package 700, the materials forming package 700, although not preferred, need not necessarily be biocompatible and one of any number of conventional ceramic material systems could be employed.

The dashed lines in FIG. 7B represent feedthrough pins 516/616 and 536/636, each of which is received in a corresponding conductive interconnect member 766, for coupling thereto, for example, by brazing. It should be noted that, although the groove may be suitable form for interconnect members 766, in order to accommodate particular arrangements of feedthrough pins within the above-described assemblies, contact/bond pads, for example, similar to pads 706, may be employed as an alternative form of interconnect members 766, which may be more suitable in some embodiments. Furthermore, the location of conductive interconnect members 766 is not limited to that illustrated in FIG. 7B, and, according to some alternate embodiments, members 766 are all located on the exterior surface of sidewall 715. In addition, it is contemplated that each interconnect member 766 may alternately be formed within a corresponding bore that extends into any of ceramic sidewalls 711-715, from an opening at the exterior surface thereof.

FIG. 7B further illustrates another sidewall 716 of package 700 formed as a lid which is hermetically sealed to a top perimeter edge 751 of sidewalls 711-714 to enclose IC chip 50 therein. According to some embodiments sidewall/lid 716 is formed of the same ceramic as sidewalls 711-715; but, according to alternate embodiments, sidewall/lid 716 is formed of a metal, such as titanium, similar to caps 65 described above. Glassing and/or brazing or diffusion bonding techniques, according to methods known in the art, may be employed to hermetically seal lid 716 to edge 751. It should be noted that the process employed to seal a metal form of lid 716 (as well as that for coupling feedthrough pins 516/616 and 536/636) should not subject IC chip 50 to a level of thermal energy that may cause damage thereto. For example, a brazed seal may be formed by a braze material that is known in the art to have a relatively low melting temperature, and a glassed seal may be formed by a glass material that is known in the art to have a relatively low melting temperature. Thermal energy for sealing may be applied according to methods known in the art, for example, by total immersion of package 700 in a furnace or oven, or by the application of localized heat with a laser of appropriate wavelength and output profile.

Upon review of the above-described switching assembly embodiments (FIGS. 5A-7B), it may be appreciated that the hermetic capsules/packages thereof may be employed to further contain any suitable sensor, such as an accelerometer, pressure sensor, temperature sensor, etc. . . . , for example, in the form of a MEMS-type transducer, and/or alternative IC chips that include any other type of suitable circuitry in addition to, or as an alternative to, multiplexer circuitry. For example, a circuit that includes a Hall effect sensor may be incorporated to detect the presence of MRI fields and then make the conductor circuits of the lead compatible therewith, according to methods known in the art. Furthermore, alternate types of standard medical electrical lead connector terminals may incorporate the above-described embodiments of hermetic capsule assemblies.

Figure 8:
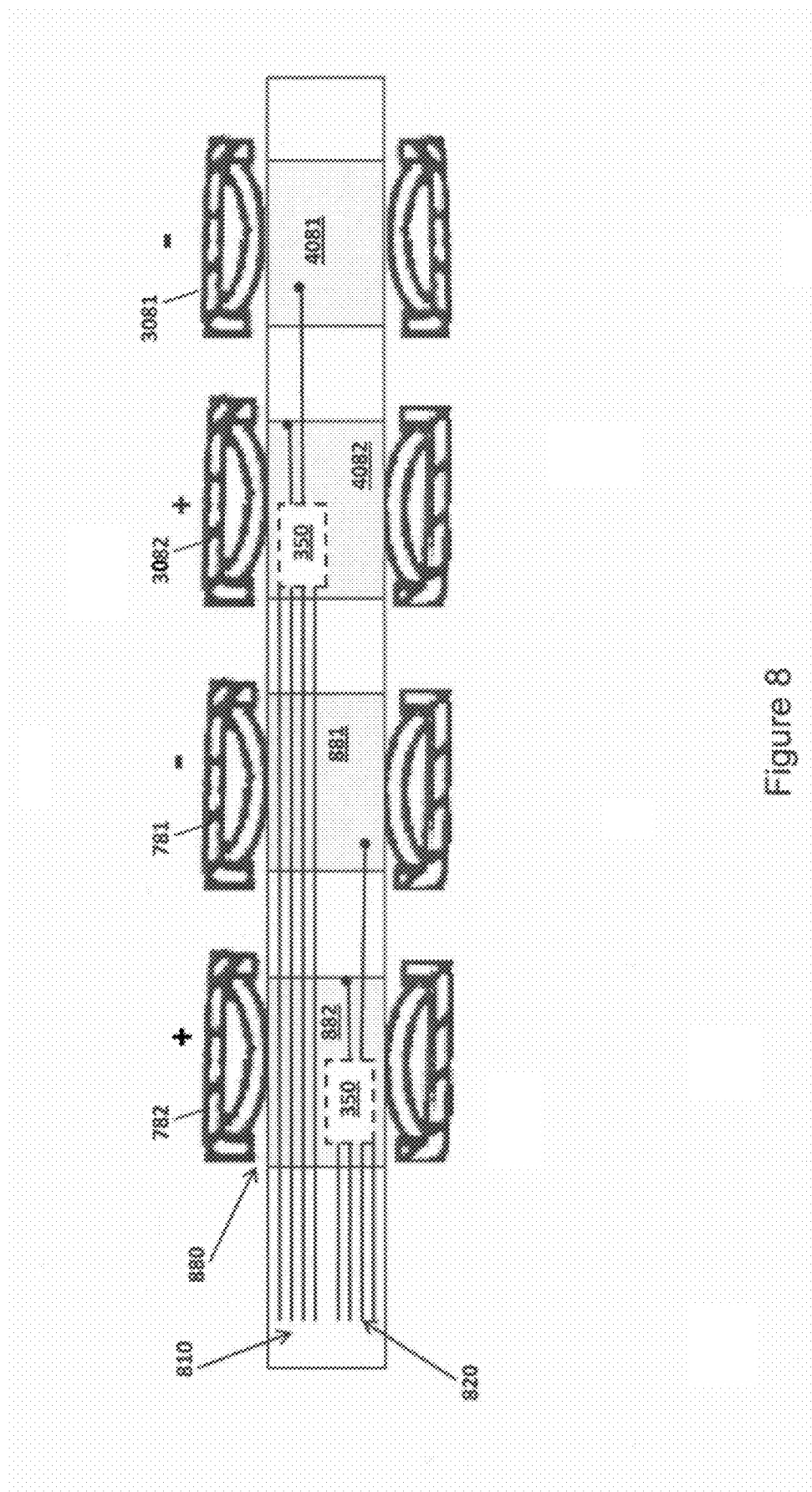
FIG. 8 is a schematic depicting a quadripolar lead connector terminal in which embodiments of the present invention may be incorporated.

With reference to the schematic of FIG. 8, a generic quadripolar connector terminal 880 is shown including two pair of bipolar contact members 4081, 4082 and 881, 882, which are spaced apart from one another along a length of the connector terminal. According to some embodiments, a slightly modified version of quadripolar connector terminal 880 conforms to what is known as the IS-4 standard for cardiac implantable medical electrical leads, wherein a volume enclosed by terminal 880 is greater than that enclosed by connector terminal 381 (FIGS. 4, 5A) so that terminal 880 can accommodate a greater number of feedthrough junctions for an enclosed hermetic capsule, for example, to provide more choices of stimulation vectors from a larger number of electrodes mounted on the corresponding lead. Furthermore, it should be noted that connector terminals complying with the IS-4 standard include two high voltage electrical contacts so that a switching assembly similar to that described above may be employed therein to select among multiple high voltage electrodes of the corresponding lead in order to deliver the most effective defibrillation shock vector. Alternately, connector 880 may be employed by an implantable neuromodulation stimulation lead that includes an array of electrodes for delivering two simultaneously applied stimulation vectors. FIG. 8 illustrates connector contact members 4081, 4082, 881, 882 each positioned for coupling to device contacts 3081, 3082, 781, 782, respectively, wherein the polarity of each device contact is established by the circuitry of the corresponding device. FIG. 8 further illustrates multiplexer 350 located in contact member 4082, in order to provide the option for selecting the coupling of any one of a plurality of lead conductors 810 to one of contact members 4081, 4082, and any other of plurality of conductors 810 to the other of contact members 4081, 4082; and another multiplexer 350 is shown located in contact member 882, in order to provide the option for selecting the coupling of any one of a plurality of lead conductors 820 to one of contact members 881, 882, and any other of plurality of conductors 820 to the other of contact members 881, 882. It should be understood that each multiplexer 350 of FIG. 8 may be part of a switching assembly, that is constructed according to any of the above-described embodiments (FIGS. 5A-7), and is enclosed within the hermetic capsule/package thereof.

In the foregoing detailed description, the invention has been described with reference to specific embodiments. However, it may be appreciated that various modifications and changes can be made without departing from the scope of the invention as set forth in the appended claims.

The invention claimed is:

1. A connector terminal for an implantable medical electrical lead, the connector terminal comprising:
    a first electrical contact member and a second electrical contact member, the second contact member being electrically isolated from the first contact member and spaced apart, distally from the first contact member along a length of the connector terminal, and the second contact member having a proximal end and a distal end; and
    a switching assembly comprising a multiplexer, a proximal feedthrough subassembly and a distal feedthrough subassembly, the multiplexer being mounted on an integrated circuit chip within the second connector contact member and electrically coupled to the second contact member, the proximal feedthrough subassembly including a conductive ferrule attached to the proximal end of the second contact member, a feedthrough pin and an insulator isolating the pin from the ferrule and being hermetically sealed to the pin and to the ferrule, the feedthrough pin electrically coupling the first contact member to the multiplexer, and the distal feedthrough subassembly including a conductive ferrule attached to the distal end of the second contact member, a plurality of feedthrough pins and an insulator isolating each of the pins from one another and from the ferrule of the distal subassembly, and being hermetically sealed to each of the pins and to the ferrule of the distal subassembly, each feedthrough pin of the distal subassembly being electrically coupled to the multiplexer and having a distal portion that extends distally from the distal end of the second contact member, the distal portions being positioned with respect to one another in order to allow for electrical coupling with a plurality of elongate conductors of the lead;
    wherein the multiplexer includes a switch matrix element and a communications, control and power supply element, the switch matrix element including a plurality of pairs of switches, each pair of the plurality of pairs of switches corresponding to one of the feedthrough pins of the distal feedthrough assembly, a first of each pair of switches being adapted to connect and disconnect the corresponding feedthrough pin to/from the first contact member and the communications, control and power supply element, and a second of each pair of switches adapted to connect and disconnect the corresponding feedthrough pin to/from the second contact member and the communications, control and power supply element; and
    each ferrule of the proximal and distal feedthrough assemblies is attached to the corresponding end of the proximal and distal ends of the second contact member by a weld that extends about an entire perimeter of the corresponding end.

2. The connector terminal of claim 1, further comprising a distal insulative support member; and wherein:
    the ferrule of the distal feedthrough subassembly includes a protrusion, which extends distally from the second contact member, and on which the distal support member is mounted;
    the distal support member includes a plurality of relatively straight channels formed in an outer surface thereof and spaced apart from one another around a circumference of the distal support member; and
    the distal portion of each distal feedthrough pin extends within a corresponding channel of the distal support member.

3. The connector terminal of claim 1, further comprising a proximal insulative support member and a conductive jumper that couples the first contact member to the proximal feedthrough pin; and wherein:
    the ferrule of the proximal feedthrough subassembly includes a protrusion, which extends proximally from the second contact member, and on which the proximal support member is mounted; and
    the conductive jumper is wrapped about the proximal support member and coupled to the proximal feedthrough pin thereon.

4. The connector terminal of claim 3, wherein:
    the proximal support member includes a relatively straight channel formed in an outer surface thereof; and
    a proximal portion of the proximal feedthrough pin extends within the channel and beneath the jumper.

5. The connector terminal of claim 1, further comprising:
    an inner wall forming a lumen that extends along the length of the connector terminal and within the second contact member, the lumen having a proximal opening in proximity to the first contact member, the inner wall isolating the lumen from the switching assembly and the aforementioned electrical couplings to the multiplexer, and at least a portion of the inner wall being formed by a tubing member;
    wherein each ferrule of the proximal and distal feedthrough assemblies includes a longitudinally extending thru-hole, the thru-holes being approximately longitudinally aligned with one another; and
    the tubing member is mounted within each thru-hole and extends within the second contact member between the ferrules.

6. The connector terminal of claim 5, wherein:
    the switching assembly further comprises a flex circuit, the flex circuit including a plurality of contact/bond pads, a plurality of connection junctions and a pair of contoured slots, one formed in each end of the flex circuit;
    the plurality of contact/bond pads being coupled to the multiplexer and to a corresponding connection junction by a conductive trace;
    each of the plurality of connection junctions being coupled to a corresponding one of the plurality of distal feedthrough pins, proximal feedthrough pins and second connector contact; and
    each contoured slot being fitted about the tubing member such that each end of the flex circuit is bent inward.

7. The connector terminal of claim 1, wherein:
    the switching assembly further comprises a ceramic insulator substrate including contact/bond pads formed on a exterior surface thereof and conductive vias formed therein, each via coupling one of the contact/bond pads to a corresponding one of the feedthrough pins and second contact member; and the integrated circuit chip is supported by the ceramic insulator substrate and coupled to the external contact/bond pads thereof.

8. The connector terminal of claim 1, wherein:

the switching assembly further comprises a package, which is contained within the second contact member and which encloses the integrated circuit chip, the package including ceramic sidewalls, conductive interconnect members formed on an exterior surface of at least one of the ceramic sidewalls, and conductive vias, each via electrically connecting the integrated circuit chip to the conductive interconnect members; and each of the distal feedthrough pins and the proximal feedthrough pin is coupled to a corresponding one of the conductive interconnect members.

9. The connector terminal of claim 8, wherein the package further includes at least one titanium sidewall.

10. The connector terminal of claim 1, wherein each insulator of the proximal and distal feedthrough subassemblies is formed of LaBor 4 glass.

11. The connector terminal of claim 1, wherein:

each ferrule of the proximal and distal feedthrough subassemblies is formed of MP35N alloy;

each feedthrough pin of the proximal and distal feedthrough subassemblies is formed of one of: Ta and Nb; and each insulator of the proximal and distal feedthrough subassemblies is formed of Ta-23 glass.

\* \* \* \* \*